United States Patent [19]

Sprecker et al.

[11] 4,289,705
[45] Sep. 15, 1981

[54] 2-OXABICYCLOOCTANE DERIVATIVE, PROCESSES FOR PREPARING SAME AND ORGANOLEPTIC USES THEREOF

[75] Inventors: Mark A. Sprecker, Sea Bright; Frederick L. Schmitt, Holmdel; Manfred H. Vock, Locust; Joaquin F. Vinals, Red Bank, all of N.J.; Jacob Kiwala, Brooklyn, N.Y.

[73] Assignee: International Flavors & Fragrances Inc., New York, N.Y.

[21] Appl. No.: 176,050

[22] Filed: Aug. 7, 1980

Related U.S. Application Data

[60] Division of Ser. No. 77,539, Sep. 21, 1979, Pat. No. 4,269,862, which is a continuation-in-part of Ser. No. 953,128, Oct. 20, 1978, Pat. No. 4,195,099.

[51] Int. Cl.$^3$ ............................................. C07D 309/04
[52] U.S. Cl. ................................................. 260/345.1
[58] Field of Search ..................................... 260/345.1

[56] References Cited

PUBLICATIONS

The Merck Index, 9th Ed., 2280 (1976).

Primary Examiner—Nicky Chan
Attorney, Agent, or Firm—Arthur L. Liberman

[57] ABSTRACT

Described is a derivative of a 2-oxabicyclo[2.2.2]octane (1,3,5,5-tetramethyl-2-oxabicyclo[2.2.2]octane) and the precursor thereof, alpha 4,6,6-tetramethyl-3-cyclohexenemethanol. The said oxabicyclooctane derivative is useful in perfumery and foodstuff, medicinal product and tobacco flavors. The cyclohexenemethanol derivative is useful as a precursor for the said oxabicyclooctane.

1 Claim, 9 Drawing Figures

GLC PROFILE FOR EXAMPLE II, FRACTION 2.

GLC PROFILE FOR EXAMPLE III, FRACTION 3.

GLC PROFILE FOR EXAMPLE III, FRACTION 2.

GLC PROFILE FOR EXAMPLE III, FRACTION 5.

GLC PROFILE FOR EXAMPLE III, FRACTION 4.

MASS SPECTRUM FOR EXAMPLE III.

NMR SPECTRUM FOR EXAMPLE III.

IR SPECTRUM FOR EXAMPLE III.

2-OXABICYCLOOCTANE DERIVATIVE, PROCESSES FOR PREPARING SAME AND ORGANOLEPTIC USES THEREOF

This is a divisional of application Ser. No. 077,539, filed Sept. 21, 1979, now U.S. Pat. No. 4,269,862, which, in turn, is a continuation-in-part of Application for U.S. Letters Patent, Ser. No. 953,128 filed Oct. 20, 1978 now U.S. Pat. No. 4,195,099 issued Mar. 25, 1980.

BACKGROUND OF THE INVENTION

The instant invention provides the novel oxabicyclooctane, 1,3,5,5-tetramethyl-2-oxabicyclo[2.2.2]octane having the structure:

as well as the alpha,4,6,6-tetramethyl-3-cyclohexenemethanol precursor therefor, having the structure:

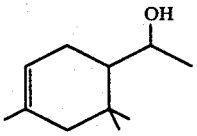

and uses of said 1,3,5,5-tetramethyl-2-oxabicyclo[2.2.2]octane for its organoleptic properties is consumable materials.

Chemical compounds which can provide minty and camphoraceous aromas with woody and piney undertones are highly desirable in the art of perfumery. Many of the natural materials which provide such fragrances and contribute such desired nuances to perfumery compositions and perfumed articles are high in cost, unobtainable at times, vary in quality from one batch to another and/or are generally subject to the usual variations of natural products.

By the same token, materials which can provide fresh camphoraceous eucalyptus oil-like and patchouli-like aromas and tastes are desirable in applying the art of flavoring to foodstuffs, toothpastes, chewing gums and medicinal products. Many of the natural materials which provide such flavor notes and contribute desired nuances to flavoring compositions are high in cost, vary in quality from one batch to another and/or are generally subject to the usual variations of natural products.

Sweet, earthy, cooling and citrus-like aromas prior to and on smoking are desirable in the tobacco art for enhancing natural tobacco-like notes.

There is, accordingly, a continuing effort to find synthetic materials which will replace, enhance or augment the essential flavor and fragrance notes provided by natural essential oils or compositions thereof. Unfortunately, many of these synthetic materials either have the desired nuances only to a relatively small degree or else contribute undesirable or unwanted odor to the compositions. The search for materials which can provide a more refined flavor for use in conjunction with cough drops or oral hygiene preparations, e.g. mouth washes, has been difficult and relatively costly in the areas of both natural products and synthetic products.

Arctander in "Perfume and Flavor Chemicals (Aroma Chemicals)", Vol. I, 1969 at monograph No. 616 describes 1,8-cineole having the structure:

as being useful in perfumery and in flavor compositions. Thus, Arctander states, regarding 1,8-cineole:

"Fresh, diffusive, camphoraceous-cool odor of poor tenacity. Sweet and fresh, cool-camphoraceous taste and cool mouthfeel unless very highly concentrated.

Widely used in perfume compositions for its refreshing effect in herbaceous type fragrances, Lavender, New Mown Hay, Fougere, etc. and in medicinal type odors for soap and household products. Also, in masking odors for industrial purposes, unless Eucalyptus oil must be used for its lower cost.

This oxide has found increased usage during the 1965/66 period of abnormally high prices for Lavandin and Spike Lavender oils.

The odor of Eucalyptus is, in some countries, rated synonomous with masking odors for lavatories, etc., a fact which has an unquestionable psychological effect, causing people to reject the odor of Eucalyuptus for oral-hygienic purposes, etc. Similar viewpoints have been observed about the use of Methylsalicylate in dentifrice in many European countries. Peculiarly enough, Methylsalicylate is still a popular candy-, soft-drink- and toothpaste flavor in the U.S.A., where the ester at the same time is used as a masking agent in toilet-bowl cleaners!

The 'olfactory association' is quite human and common, but it may at times completely destroy the chances of a chemical from its use in flavors or other field.

Eucalyptol is extensively used in flavor compositions, particularly in all types of preparations for oral hygiene, dentifrice, breath-sprays, mouthwashes, cough lozenges, pastilles, skin-rubbing lotions, inhalator fluids, etc.

It seems, however, that its use in skin rubbing lotions has hampered its popularity as a candy flavor in the U.S.A.

Normal use concentrations are about 1 to 15 ppm in the finished (flavored) product, but concentrations as high as 200 ppm are found in chewing gum."

Furthermore, the compound having the structure:

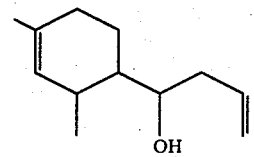

and the compound having the structure:

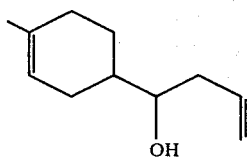

are reported by Sopov and Kovner at Zh. Obsch. Khim. 34, 1492-6 (1964) as abstracted in Chem. Abstracts, Vol. 61, 5529b.

The Sopov and Kovner reference does not, however, disclose organolepltic uses of the compounds having the structures:

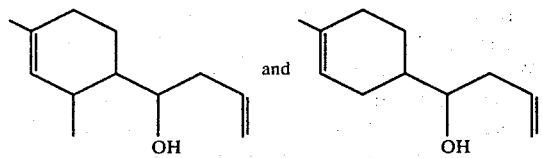

Furthermore, nothing in the prior art discloses any of the compounds having the generic structure:

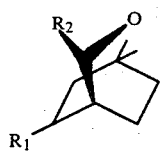

wherein R₂ is C₃–C₅ alkyl or alkenyl and R₁ is hydrogen or methyl and nothing in the prior art discloses organoleptic uses or uses as intermediates of the compound having the structure:

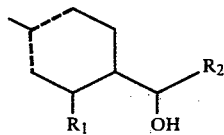

wherein R₁ is hydrogen or methyl and R₂ is C₃–C₅ alkyl or alkenyl, or lower alkyl esters thereof, e.g., acetates.

Insofar as its organoleptic properties are concerned, the compound of the instant invention, 1,3,5,5-tetramethyl-2-oxabicyclo[2.2.2]octane, has unexpected, unobvious and advantageous properties over compounds of the prior art such as 1,8-cineole.

THE INVENTION

Figure 1:
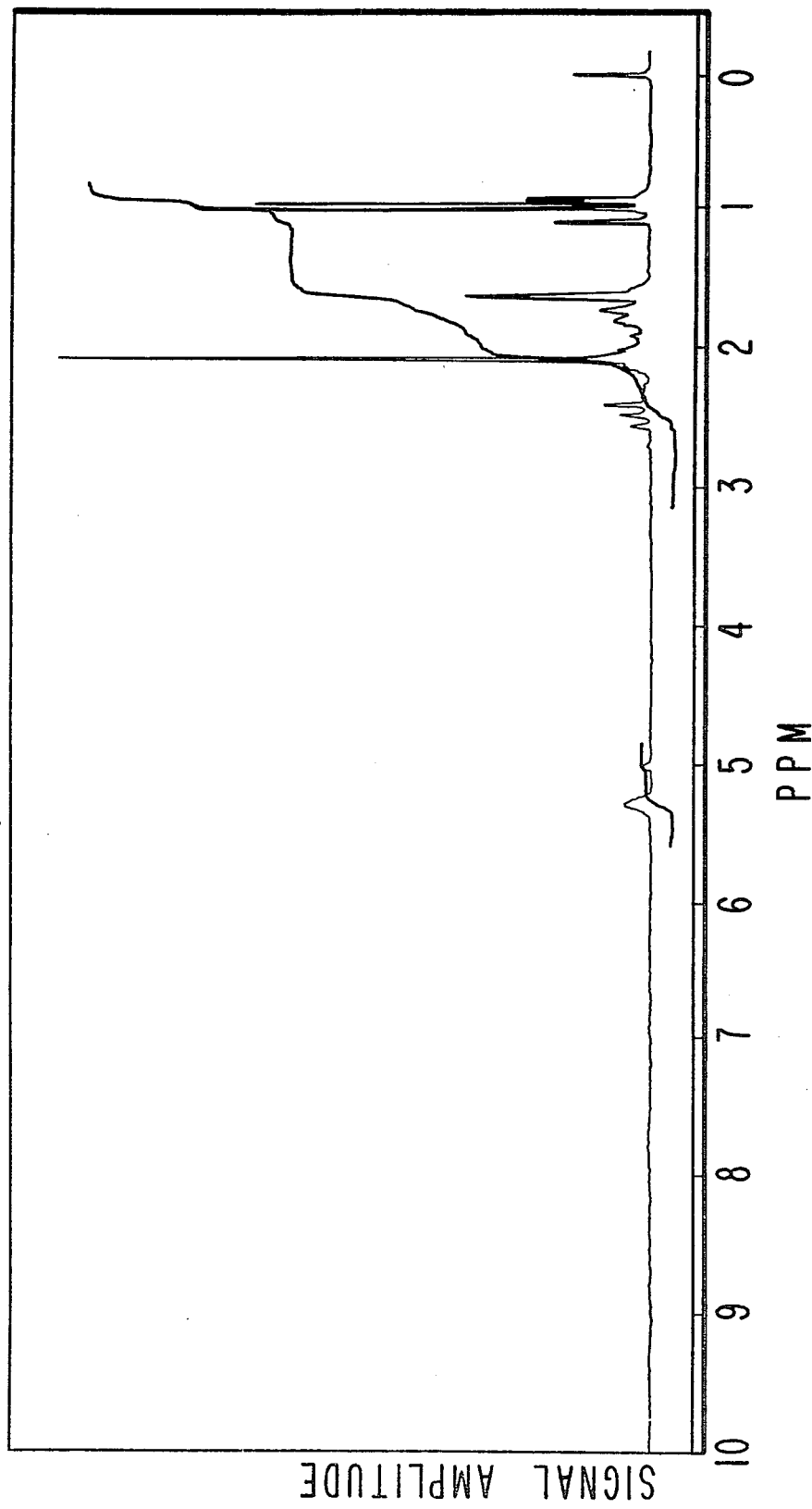
FIG. 1 is the NMR spectrum for alpha,4,6,6-tetramethyl-3-cyclohexenemethanol produced according to Example I (fraction 13).

It has now been determined that 1,3,5,5-tetramethyl-2-oxabicyclo[2.2.2]octane is capable of imparting a variety of flavors and fragrances to various consumable materials and is also capable of augmenting or enhancing a variety of flavors and fragrances of various consumable materials.

Briefly, our invention contemplates augmenting or enhancing the flavors and/or fragrances of such consumable materials as perfumes, perfumed articles, colognes, foodstuffs, chewing gums, toothpastes, medicinal products and smoking tobaccos by adding thereto a small but effective amount of 1,3,5,5-tetramethyl-2-oxabicyclo[2.2.2]octane having the structure:

1,3,5,5-tetramethyl-2-oxabicyclo[2.2.2]octane of our invention augments or enhances fresh camphoraceous eucalypltus-like, patchouli-like aroma and taste characteristics of foodstuffs, toothpastes, medicinal products and chewing gums.

1,3,5,5-tetramethyl-2-oxabicyclo[2.2.2]octane of our invention also augments or enhances the minty, camphoraceous, woody and piney aromas of perfumes, perfumed articles and colognes of our invention.

1,3,5,5-tetramethyl-2-oxabicyclo[2.2.2]octane of our invention also augments or enhances the sweet, earthy, cooling, citrus-like characteristics of smoking tobacco by imparting thereto sweet, earthy, cooling, citrus-like aroma and taste nuances prior to and on smoking in the mainstream and in the sidestream of smoking tobacco articles.

1,3,5,5-tetramethyl-2-oxabicyclo[2.2.2]octane of our invention can be produced by first forming 2,2,4-trimethyl-4-cyclohexene-1-carboxaldehyde by reaction of an alpha, beta unsaturated aldehyde with a conjugated diene; in this case, 3-methyl-2-butenal with isoprene. The resulting cyclohexene carboxaldehyde is then reacted with methyl magnesium halide (a Grignard reagent) to form an organometallic salt of a cyclohexene carbinol having the structure:

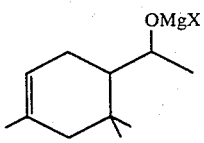

The organometallic salt of the cyclohexene carbinol is then hydrolyzed (in the presence of acid) to form the compound having the structure:

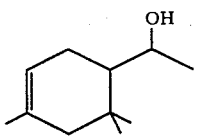

This reaction product is then further reacted by cyclizing the compound to form 1,3,5,5-tetramethyl-2-oxabicyclo[2.2.2]octane The over-all reaction sequence described above is as follows:

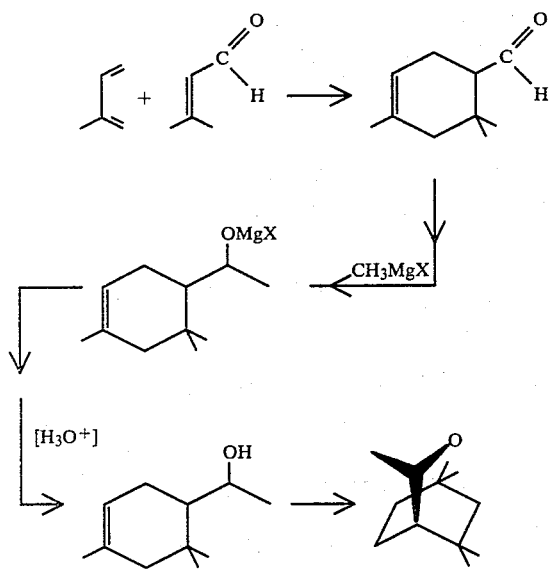

wherein X is chloro, bromo or iodo.

The Diels-Alder reaction of the alpha, beta-unsaturated aldehyde (the 3-methyl-2-butenal) with the conjugated diene (isoprene) is a procedure well known in the prior art. The reaction may be carried out in the presence of Lewis acid catalysts such as zinc chloride, aluminum chloride or aluminum bromide; or it may be carried out in the absence of catalysts at higher temperatures, e.g., 50° C. up to 150° C. When carrying out the Diels-Alder reaction in the presence of catalysts, lower temperatures, e.g., −10° C. up to 30° C. may be utilized.

That part of the reaction sequence whereby the cyclohexene carboxaldehyde (the 2,2,4-trimethyl-4-cyclohexene-1-carboxaldehyde) is reacted with the Grignard reagent (methyl magnesium halide) to form the cyclohexene carbinol organometallic salt having the structure:

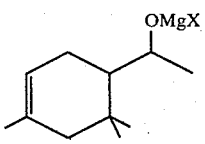

followed by hydrolysis of the cyclohexene carbinol organometallic salt to form the cyclohexene carbinol having the structure:

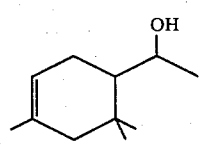

followed by cyclization of the resulting cyclohexene carbinol to form 1,3,5,5-tetramethyl-2-oxabicyclo[2.2.2]octane having the structure:

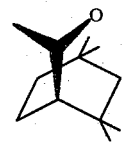

may be carried out either in one step or in two steps.

In carrying out the "two-step reaction" whereby the cyclohexene carbinol is first isolated and then cyclized in the first step, that is, in the reaction of the Grignard reagent with the cyclohexene carboxaldehyde, the mole ratio of alkyl halide or alkenyl halide to magnesium in order to form the Grignard reagent is from 0.9:1 up to 1.5:1. The mole ratio of alkyl halide or alkenyl halide to cyclohexene carboxaldehyde is from 0.8:1 up to 1.5:1. This reaction of the Grignard reagent with the cyclohexene carboxaldehyde takes place in an ether solvent such as diethyl ether, tetrahydrofuran or di-n-butyl ether or another inert solvent such as toluene, chloroform or benzene to which two equivalents of ether has been added. The temperature of reaction preferably is between 0° and 100° C. with the most preferred temperature range for this reaction being from 35° C. up to 45° C.

In the two-step reaction, the resulting cyclohexene carbinol is then isolated as by distillation. The resulting cyclohexene carbinol is then cyclized at a temperature in the range of from 25° C. up to 150° C. in the presence of an acid such as aqueous hydrochloric acid or sulfuric acid or phosphoric acid. This acid may be used in combination with an alcohol such as isopropyl alcohol or with some other solvents such as tetrahydrofuran or acrylonitrile or the acid may be used by itself to effect the cyclization. The cyclization in the alternative may be carried out using a Lewis Acid such as borontrifluoride, aluminum trichloride, zinc chloride, stannic chloride or zinc bromide in the presence of a solvent such as toluene, chloroform or xylene.

As stated above, the reaction of the cyclohexene carboxaldehyde to form the cyclohexene carbinol followed by cyclization may take place in a single reactor without separation of the cyclohexene carbinol. The conditions are the same as stated above for the two-step reaction.

In the alternative, the 1,3,5,5-tetramethyl-2-oxabicyclo[2.2.2]octane of our invention may be prepared by reacting mesitylene oxide with isoprene to form 1-acetyl-2,2,4-trimethyl-4-cyclohexene according to the reaction sequence:

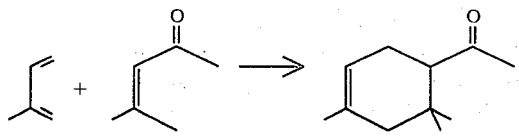

The resulting acetyl cyclohexene derivative may then be reduced to form the 1-(1''-hydroxyethyl)2,2,4-trimethyl-4-cyclohexene according to the reaction:

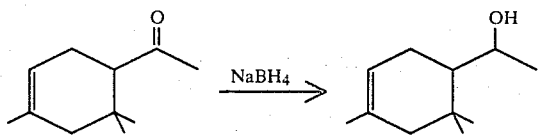

The resulting cyclohexene carbinol derivative may then be cyclized according to the reaction:

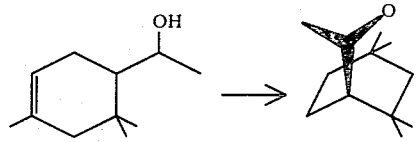

The Diels-Alder reaction of the alpha, beta-unsaturated ketone with the conjugated diene (isoprene) is a procedure well known in the prior art. The reaction may be carried out in the presence of Lewis acid catalysts such as zinc chloride, aluminum chloride or aluminum bromide; or it may be carried out in the absence of catalysts at higher temperatures, e.g., 50° C. up to 150° C. When carrying out the Diels-Alder reaction in the presence of catalysts, lower temperatures, e.g., −10° C. up to 30° C. may be utilized.

The resulting 4-acetyl-1,3,3-trimethyl-1-cyclohexene is then reduced to form the alpha,4,6,6-tetramethyl-3-cyclohexenemethanol using an alkali metal borohydride such as sodium borohydride in the presence of an inert solvent such as anhydrous ethanol or isopropyl or anhydrous methanol. The reaction is carried out at temperatures of between 20° C. up to about 50° C. for a period of time of from about two hours up to about ten hours. The weight ratio of alkali metal borohydride:4-acetyl-1,3,3-trimethyl-1-cyclohexene is about from 1:20 up to about 1:5 with a ratio of alkali metal borohydride:4-acetyl-1,3,3-trimethyl-1-cyclohexene of 1:12 being preferred and a reaction temperature of from 25° C. up to 45° C. being preferred. The concentration of 4-acetyl-1,3,3-trimethyl-1-cyclohexene in solvent may vary from about 1 part cyclohexene derivative:0.5 parts solvent up to 1 part cyclohexene derivative:4 parts solvent with a preferred ratio of 180 grams of cyclohexene derivative:100 ml isopropanol.

The resulting cyclohexene carbinol is then cyclized at a temperature in the range of from 25° C. up to 150° C. in the presence of an acid such as aqueous hydrochloric acid or sulfuric acid or phosphoric acid. This acid may be used in combination with an alcohol such as isopropyl alcohol or with some other solvents such as tetrahydrofuran or acrylonitrile or the acid may be used by itself to effect the cyclization. The cyclization, in the alternative, may be carried out using a Lewis Acid such as borontrifluoride, aluminum trichloride, zinc chloride, stannic chloride or zinc bromide in the presence of a solvent such as toluene, chloroform or xylene.

The reaction sequence for this second series of reactions using mesitylene oxide as a precursor is set forth as follows:

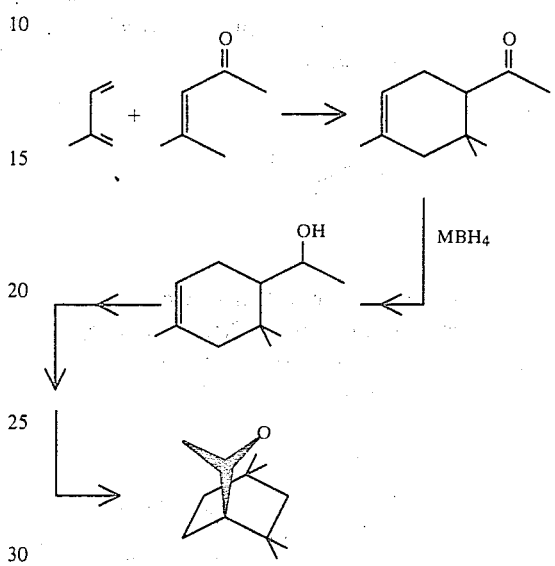

wherein M is an alkali metal such as sodium, lithium, or potassium.

The individual 1,3,5,5-tetramethyl-2-oxabicyclo[2.2.2]octane of our invention can be obtained in pure form or in substantially pure form by conventional purification techniques. Thus, 1,3,5,5-tetramethyl-2-oxabicyclo[2.2.2]octane can be purified and/or isolated by distillation, extraction, crystallization, preparative chromatographic techniques (column chromatography and vapor phase chromatography) and the like. It has been found desirable to purify the 1,3,5,5-tetramethyl-2-oxabicyclo[2.2.2]octane of our invention by fractional distillation in vacuo.

When the 1,3,5,5-tetramethyl-2-oxabicyclo[2.2.2]octane of our invention is used as a food flavor adjuvant, the nature of the co-ingredients included with said 1,3,5,5-tetramethyl-2-oxabicyclo[2.2.2]octane in formulating the product composition will also serve to alter, modify, augment or enhance the organoleptic characteristics of the ultimate foodstuff treated therewith.

As used herein in regard to flavors, the terms "alter", "modify" and "augment" in their various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks, and the like.

As used herein, the term "medicinal product" includes both solids and liquids which are ingestible, non-toxic materials which have medicinal value such as cough syrups, cough drops, aspirin and chewable medicinal tablets.

The term "chewing gum" is intended to mean a composition which comprises a substantially water insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine, and a flavoring composition which incorporates 1,3,5,5-tetramethyl-2-oxabicyclo[2.2.2]octane of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterised as flavoring adjuvants or vehicles comprising, broadly, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxy anisole), butylated hydroxytoluene (2,6-di-tertiary-butyl-4-methyl phenol), propyl gallate and the like, sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates; starches, pectins, and emulsifiers, e.g., mono- and diglycerides of fatty acids, skim milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like, firming agents such as aluminum sodium sulfate, calcium chloride and calcium gluconate; texturizers, anticaking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alphamethylbutyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methylbutanal, beta,-beta-dimethyl acrolein, methyl n-amyl ketone, n-hexanal, 2-hexenal, isopentanal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, beta-damascone, alpha-damascone, beta-damascenone, acetophenone, 2-heptanone, o-hydroxy-acetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methylfurfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpinhydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl carpylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate, and terpenyl acetate; hydrocarbons such as dimethyl naphthalene, dodecane, methyldiphenyl, methyl naphthalene, myrcene, naphthalene, octadecane, tetradecane, tetramethylnaphthalene, tridecane, trimethylnaphthalene, undecane, caryophyllene, alphaphellandrene, beta-phellandrene, p-cymene 1-alpha-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essential oil, safran oil, Bulgarian rose, capsicum, yara yara and vanilla; lactones such as γ-nonalactone; sulfides, e.g., methyl sulfide and other materials such as maltol, and acetals (e.g., 1,1-diethoxyethane, 1,1-dimethyloxyethane and dimethoxymethane), piperine, chavicine, and piperidine.

The specific flavoring adjuvant selected for use may be either solid or liquid depending upon the desired physical form of the ultimate product, i.e., foodstuff, whether simulated or natural, and should, in any event, (i) be organoleptically compatible with 1,3,5,5-tetramethyl-2-oxabicyclo[2.2.2]octane of our invention by not covering or spoiling the organoleptic properties (aroma and/or taste) thereof; (ii) be non-reactive with 1,3,5,5-tetramethyl-2-oxabicyclo [2.2.2]octane of our invention and (iii) be capable of providing an environment in which 1,3,5,5-tetramethyl-2-oxabicyclo [2.2.2]octane can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of 1,3,5,5-tetramethyl-2-oxabicyclo [2.2.2]octane employed in a particular instance can vary over a relatively wide range, depending upon the desired organoleptic effects to be achieved. Thus, correspondingly, greater amounts would be necessary in those instances wherein the ultimate food composition to be flavored (e.g., with a eucalyptus oil-like flavor) is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, or flavoring composition. The use of insufficient quantities of 1,3,5,5-tetramethyl-2-oxabicyclo [2.2.2]octane will, of course, substantially vitiate any possibility of obtaining the desired results while excess quantities prove needlessly costly and in extreme cases may disrupt the flavor-aroma balance, thus proving selfdefeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of 1,3,5,5-tetramethyl-2-oxabicyclo [2.2.2]octane ranging from a small but effective amount, e.g., 0.02 parts per million up to about 500 parts per million based on total composition, are suitable. Concentrations in excess of the maximum quantity stated are not normally recommended since they fail to provide commensurate enhancement of organoleptic properties. In those instances wherein 1,3,5,5-tetramethyl-2-oxabicyclo [2.2.2]octane is added to the foodstuff as an integral component of a flavoring composition, it is, of course, essential that the total quantity of flavoring composition employed be sufficient to yield an effective 1,3,5,5-tetramethyl-2-oxabicyclo [2.2.2]octane concentration in the foodstuff product.

Food flavoring compositions prepared in accordance with the present invention preferably contain 1,3,5,5-tetramethyl 2-oxabicyclo [2.2.2]octane in concentrations ranging from about 0.025% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing 1,3,5,5-tetramethyl-2-oxabicyclo [2.2.2]octane with, for example, gum arabic, gum tragacanth, carrageenan and the like, and thereafter spray-drying the resultant mixture whereby to obtain the particular solid product. Pre-prepared flavor mixes in powder form, e.g., a eucalyptus oil flavored powder mix, are obtained by mixing the dried solid components, e.g., starch, sugar and the like, and 1,3,5,5-tetramethyl-2-oxabicyclo [2.2.2]octane in a dry blender until the requisite degree of uniformity is achieved.

It is presently preferred to combine with 1,3,5,5-tetramethyl-2-oxabicyclo [2.2.2]octane of our invention, the following adjuvants: Oil of Cubeb; Phellandrene; beta-Phellandrene; Oil of Coriander; Oil of Pimento Leaf, Oil of Patchouli; Natural Lemon Oil; Acetaldehyde; α-Terpineol; Citral; Carvone; Terpinolene; α-Terpinene; Diphenyl; α-Fenchyl Alcohol; Cineole; Limonene; Linalool; Geranyl Acetate; Nootkatone; Neryl Acetate; Heliotropin; Maltol, Vanillin; Ethyl Maltol; Ethyl Vanillin; Anisaldehyde; Alpha Pinene; Beta-Pinene; Beta-Caryophyllene; Dihydrocarveol; Piperonal; Piperine; Chavicine; Piperidine; Oil of Black Pepper; Black Pepper Oleoresin; Capsicum; Oil of Nutmeg; Cardamom Oil; Clove Oil; Separmint Oil; Oil of Peppermint; and $C_{10}$-Terpinyl Ethers as described in application for U.S. Letters Patent, Ser. No. 872,937 filed on Jan. 27, 1978, now U.S. Pat. No. 4,131,687 issued on Dec. 26, 1978. (such as fenchyl ethyl ethers).

The 1,3,5,5-tetramethyl-2-oxabicyclo [2.2.2]octane of our invention can be used to contribute minty and camphoraceous notes with woody and piney undertone to perfumes, perfumed articles and colognes. Examples of such perfumed articles are dryer-added fabric softener articles and liquid or solid cationic, anionic or non-ionic detergents. As olfactory agents, the 1,3,5,5-tetramethyl-2-oxabicyclo [2.2.2]octane of our invention can be formulated into or used as components of a "perfume composition" or can be used as components of a "perfumed article" or the perfume composition may be added to perfumed articles.

The term "perfume composition" is used herein to mean a mixture of organic compounds including, for example, alcohols, aldehydes, ketones, nitriles, ethers, lactones, natural essential oils, synthetic essential oils and frequently hydrocarbons which are admixed so that the combined odors of the individual components produce a pleasant or desired fragrance. Such perfume compositions usually contain: (a) the main note or the "bouquet" of foundationstone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling, fresh-smelling materials.

In perfume compositions, the individual component will contribute its particular olfactory characteristics, but the overall effect of the perfume composition will be the sum of the effects of each of the ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of 1,3,5,5-tetramethyl-2-oxabicyclo [2.2.2]octane of this invention which will be effective in perfume compositions depends on many factors, including the other ingredients, their amounts and the effects which are desired. It has been found that perfume compositions containing as little as 0.5% of 1,3,5,5-tetramethyl-2-oxabicyclo [2.2.2]octane of this invention, or even less, can be used to impart an interesting minty, herbaceous and/or anise-like aroma to soaps, liquid and solid cationic, anionic and nonionic detergents, cosmetics, powders, liquid and solid fabric softeners, optical brightener compositions, and other products. The amount employed can range up to 50% or higher and will depend on considerations of cost, nature of the end product, and the effect desired on the finished product and particular fragrance sought.

The 1,3,5,5-tetramethyl-2-oxabicyclo [2.2.2]octane of this invention can be used alone or in a perfume composition as an olfactory component in detergents and soaps, space odorants and deodorants; perfumes; colognes, toilet waters; bath salts; hair preparations such as lacquers, brilliantines, pomades, and shampoos; cosmetic preparations such as creams, deodorants, hand lotions, and sun screens; powders such as talcs, dusting powders, face powder, and the like. When used as an olfactory component of a perfumed article, as little as 0.01% of 1,3,5,5-tetramethyl-2-oxabicyclo [2.2.2]octane will suffice to impart an interesting minty, herbaceous and/or anise-like aroma. Generally no more than 0.5% is required.

In addition, the perfume composition can contain a vehicle or carrier for 1,3,5,5-tetramethyl-2-oxabicyclo [2.2.2]octane alone or with other ingredients. The vehicle can be a liquid such as an alcohol such as ethanol, a glycol such as propylene glycol, or the like. The carrier can be an absorbent solid such as a gum or components for encapsulating the composition such as gelatin which can be used to form a capsule wall surrounding the perfume oil, by means of coacervation.

An additional aspect of our invention provides an organoleptically improved smoking tobacco product and additives therefor including methods of making the same which overcome problems heretofore encountered in the creation or enhancement of specific desired sweet, earthy, cooling and citrus-like notes, both prior to and on smoking, in both the main stream and the side stream, may now be readily controlled and maintained at the desired uniform level regardless of variations in the tobacco components of the blend; or the nature of the filter used in conjunction with the smoking tobacco article.

This invention further provides improved tobacco additives and additives for materials used in the fabrication of tobacco articles (particularly smoking tobacco articles) and methods whereby desirable hay-like notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient, 1,3,5,5-tetramethyl-2-oxabicyclo [2.2.2]octane of our invention.

In addition to 1,3,5,5-tetramethyl-2-oxabicyclo [2.2.2]octane of our invention, other flavoring and aroma additives may be added to the smoking tobacco material or substitute therefor either separately or in mixture with 1,3,5,5-tetramethyl-2-oxabicyclo [2.2.2]octane of our invention:

I. Synthetic Materials

Beta-methylcinnamaldehyde;
Eugenol;
Dipentene;
Damascenone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexen-1-ol;
2-Methyl-5-isopropyl-1,3-nonadiene-8-one;
2-Methyl-5-isopropylacetophenone;
2-Hydroxy-2,5,5,8α-tetramethyl-1-)2-hydroxyethyl)-decahydronaphthalene;
Dodecahydro-3α,6,6,9α-tetramethylnaphtho (2,1-β)-furan;
4-Hydroxyhexenoic acid, gamma-lactone;
Polyisoprenoid hydrocarbons defined in Example V of U.S. Pat. No. 3,589,372 issued on June 29, 1971

II. Natural Oils

Celery seed oil;
Coffee extract;
Bergamot oil;
Cocoa extract;
Nutmeg oil;
Origanum oil.

An aroma and flavoring concentrate containing 1,3,5,5-tetramethyl-2-oxabicyclo [2.2.2]octane of our invention and, if desired one or more of the above-indicated additional flavoring additives may be added to the smoking tobacco material, to the filter or to the leaf or paper wrapper or to a filter which is part of the smoking article. The smoking tobacco material may be shredded, cured, cased and cured, cased and blended tobacco material or reconstituted tobacco material or tobacco substitutes (e.g., lettuce leaves) or mixtures thereof. The proportions of flavoring additives may be varied in accordance with taste, but insofar as enhancement or the imparting of hay-like notes prior to and on smoking, in both the main stream and the side stream, we have found that satisfactory results are obtained if the proportion by weight of the sum total of 1,3,5,5-tetramethyl-2-oxabicyclo [2.2.2]octane to smoking tobacco material is between 50 ppm and 1500 ppm (0.005%–0.15%) of the active ingredients to the smoking tobacco material. We have further found that satisfactory results are obtained if the proportions by weight of the sum total of 1,3,5,5-tetramethyl-2-oxabicyclo

[2.2.2]octane used to flavoring material is between 0.05:1 and 0.50:1.

Any convenient method for incorporating 1,3,5,5-tetramethyl 2-oxabicyclo [2.2.2]octane in the tobacco product may be employed. Thus 1,3,5,5-tetramethyl-2-oxabicyclo [2.2.2]octane taken alone or along with other flavoring additives may be dissolved in a suitable solvent such as food grade ethanol, pentane, diethyl ether and/or other volatile organic solvents, and the resulting solution may either be sprayed on the cured, cased and blended tobacco material; or the tobacco material or filter may be dipped into such solution. Under certain circumstances, a solution of 1,3,5,5-tetramethyl-2-oxabicyclo [2.2.2]octane taken alone or taken further together with other flavoring additives as set forth above, may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated, and the thus-treated tobacco may be blended with other tobaccos before the ultimate tobacco product is formed. In such cases, the tobacco treated may have 1,3,5,5-tetramethyl-2-oxabicyclo [2.2.2]octane of our invention in excess of the amounts or concentrations above indicated so that when blended with other tobaccos, the final product will have the percentage within the indicated range.

While our invention is particularly useful in the manufacture of smoking tobacco such as cigarette tobacco, cigar tobacco and pipe tobacco, other tobacco products formed from sheeted tobacco dust or fines may also be used. As stated supra, 1,3,5,5-tetramethyl-2-oxabicyclo [2.2.2]-octane of our invention can be incorporated with materials such as filter tip materials, seam paste, packaging materials and the like which are used along with the tobacco to form a product adapted for smoking. Furthermore, 1,3,5,5-tetramethyl-2-oxabicyclo [2.2.2]octane of our invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of tobacco plant parts or substitute materials or both.

It will thus be apparent that 1,3,5,5-tetramethyl-2-oxabicyclo [2.2.2]octane of our invention can be utilized to alter, modify, augment or enhance sensory properties, particularly organoleptic properties, such as flavor(s) and/or fragrance(s) of a wide variety of consumable materials.

The following examples serve to illustrate our invention, and this invention is to be considered restricted thereto only as indicated in the appended claims.

All parts and percentages given herein are by weight unless otherwise specified.

EXAMPLE I

PREPARATION OF 4-ACETYL-1,3,3-TRIMETHYL-1-CYCLOHEXENE

Reaction:

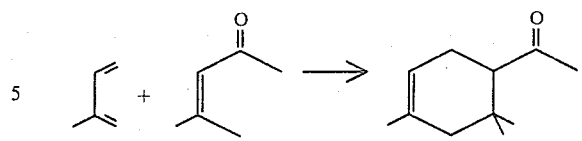

Mesityl oxide (441 g) is added at 12°–16° C. to a stirred suspension of aluminum chloride (63 g) in toluene (2100 ml). A solution of isoprene (1224 g) in toluene (1800 ml) is then added over a period of 1.5 hr. at 15°–20° C. After approximately 48 hr. at 15°–25° C., the reaction mixture is washed successively with 10% hydrochloric acid sollution, water, 10% sodium bicarbonate solution, and water. The washed material is distilled rapidly at 3 mm Hg using a short column to give 626 g of crude product. Fractionation of 548 g of this material through a 12"×1", Goodloe packed column gives 478 g of 4-acetyl-1,3,3-trimethyl-1-cyclohexene containing a small amount of 1,8-p-menthadiene. The structure is confirmed by NMR ($^1$H and $^{13}$C).

The distillation using a 2" Splash Column with Saddles is as follows:

| No. | Vapor Temp. | Liquid Temp. | Vac. mm Hg | Wgt. Fract. |
|---|---|---|---|---|
| 1 | 71 | 85 | 2.8 | 45.2 |
| 2 | 71 | 85 | 3.2 | 43.8 |
| 3 | 71 | 85 | 3.2 | 44.9 |
| 4 | 71 | 85 | 3.0 | 49.1 |
| 5 | 70 | 85 | 3.0 | 46.3 |
| 6 | 70 | 85 | 3.0 | 48.3 |
| 7 | 71 | 87 | 3.0 | 45.9 |
| 8 | 72 | 89 | 3.0 | 45.8 |
| 9 | 73 | 96 | 3.0 | 91.2 |
| 10 | 78 | 120 | 3.0 | 89.2 |

Then fractions 1–10 were bulked and distilled using a 12" Silver Mirror Goodloe Column:

| No. | Vapor Temp. | Liquid Temp. | Vac. mm Hg | Reflux Ratio R/D | Wgt. Fract. |
|---|---|---|---|---|---|
| 1 | 40/41 | 64/64 | .80/.80 | 9:1/9:1 | 21.1 |
| 2 | 46 | 65 | .80 | 9:1 | 20.3 |
| 3 | 48 | 65 | 1.0 | 9:1 | 17.8 |
| 4 | 49 | 65 | 1.0 | 9:1 | 16.6 |
| 5 | 49 | 66 | 1.0 | 9:1 | 21.5 |
| 6 | 49 | 66 | 1.0 | 9:1 | 24.0 |
| 7 | 50 | 66 | 1.0 | 9:1 | 19.4 |
| 8 | 50 | 66 | 1.0 | 9:1 | 40.6 |
| 9 | 50 | 66 | 1.0 | 9:1 | 39.0 |
| 10 | 50 | 67 | 1.0 | 9:1 | 45.7 |

FIG. 1 sets forth the NMR spectrum for fraction 13.

EXAMPLE II

PREPARATION OF ALPHA, 4,6,6-TETRAMETHYL-3-CYCLOHEXENEMETHANOL

Reaction:

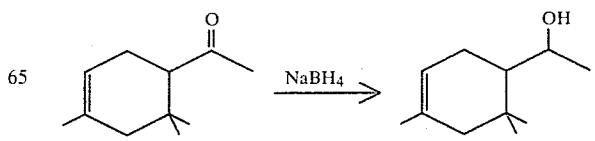

4-Acetyl-1,3,3-trimethyl-1-cyclohexene (180 g), prepared according to Example I, is added to a mixture of 15 g of sodium borohydride and 100 ml of isopropanol over a period of 6 hours at 20°–30° C. Methanol (45 ml) is added after 2 hr. feed time to facilitate the reaction. The mixture is stirred at 25°–45° C. with methanol added at intervals until GLC analysis indicates complete reduction. The mixture is poured into a mixture of dilute hydrochloric acid and crushed ice and is washed well with water. Rapid distillation through a short column gives 121 g of material, b.p. 70° C./0.2 mm Hg.

The fractionation data is as follows:

| No. | Vapor Temp. | Liquid Temp. | Vac. mm Hg | Wgt. Fract. |
| --- | --- | --- | --- | --- |
| 1 | 47 | 64 | .2 | 15.3 |
| 2 | 70 | 140 | 0.2 | 121.0 |
| 3 | 97 | 210 | 0.2 | 4.5 |

Figure 2:
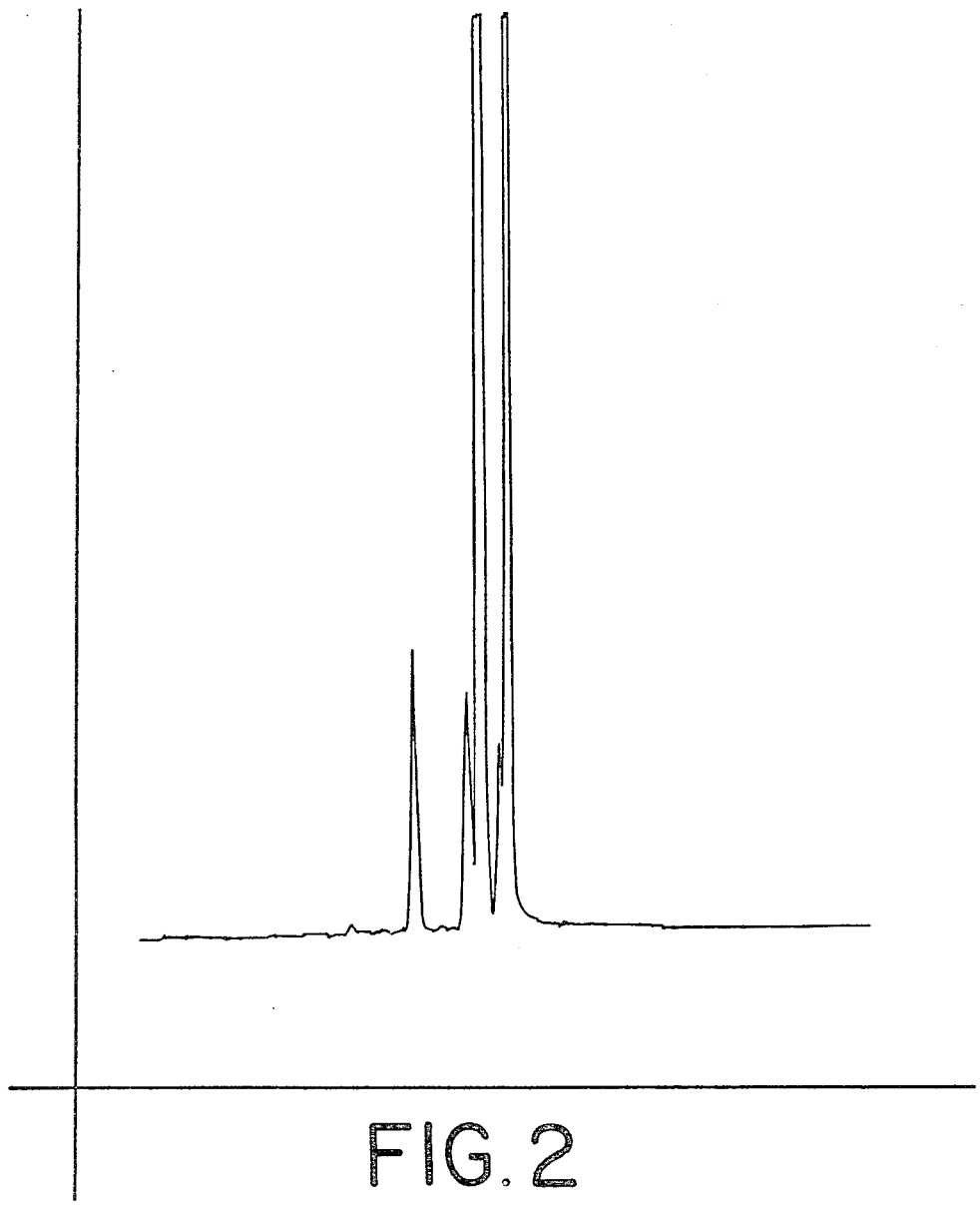
FIG. 2 is the GLC profile for fraction 2 of the reaction product produced according to Example II containing alpha,4,6,6-tetramethyl-3-cyclohexenemethanol.

FIG. 2 sets forth the GLC profile for fraction 2 prepared according to this example.

EXAMPLE III

PREPARATION OF 1,3,5,5-TETRAMETHYL-2-OXABICYCLO [2.2.2]OCTANE

Reaction:

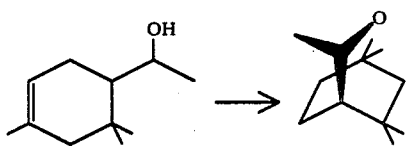

Into a 500 ml reaction flask equipped with reflux head, thermometer and stirrer is added 50 g of 40% sulfuric acid and 50 g of anhydrous isopropyl alcohol. The resulting mixture is heated to reflux and 1,3,3-trimethyl-1-cyclohexene-4-ethanol, prepared according to Example II (50 g) (fraction 2 according to Example II) is added slowly to the reaction mass while maintaining the temperature thereof at 86°–88° C. The addition takes place over a period of one hour. At the end of the addition of the cyclohexene derivative, the reaction mass is cooled to room temperature and water is added. The reaction mass now exists in two phases. The phases are separated and the organic phase is washed with aqueous sodium carbonate and saturated sodium chloride. The organic phase is then distilled using a microdistillation set-up (micro Vigreux column) yielding the following fractions:

| No. | Vapor Temp. | Liquid Temp. | Vac. mm Hg | Wgt. Fract. |
| --- | --- | --- | --- | --- |
| 1 | 55/59 | 80/83 | 18/18 | 1.5 |
| 2 | 65 | 104 | 30 | 2.2 |
| 3 | 69 | 104 | 30 | 3.3 |
| 4 | 70 | 106 | 30 | 3.6 |
| 5 | 67 | 108 | 30 | 3.0 |
| 6 | 68 | 108 | 30 | 3.9 |
| 7 | 60 | 112 | 30 | 4.6 |
| 8 | 40 | 113 | 30 | 5.0 |
| 9 | 81 | 117 | 15 | 7.8 |
| 10 | 60 | 135 | 12 | 6.2 |

NMR, IR and mass spectral analysis yield the information that the reaction product has the structure:

Figure 4:
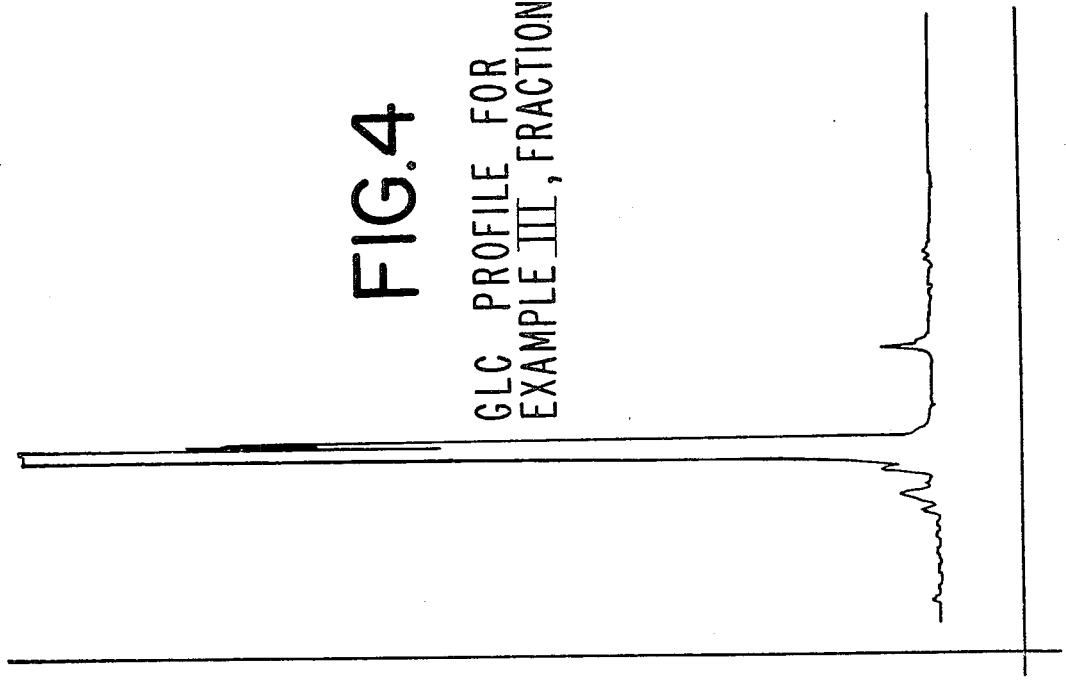
FIG. 4 is the GLC profile for fraction 3 produced according to Example III containing 1,3,5,5-tetramethyl-2-oxabicyclo[2.2.2]octane.
Figure 3:
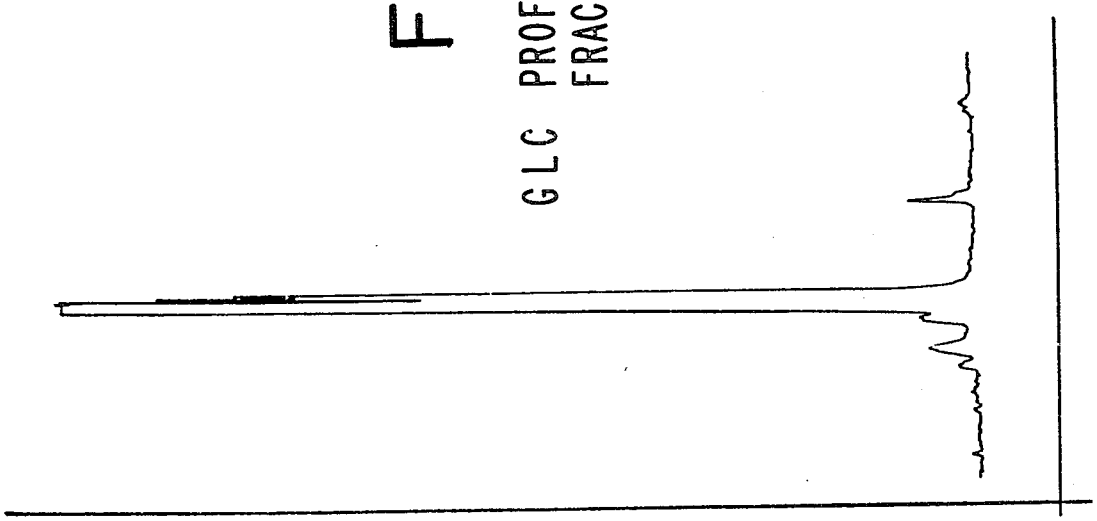
FIG. 3 is the GLC profile for fraction 2 of the product produced according to Example III, 1,3,5,5-tetramethyl-2-oxabicyclo[2.2.2]octane.
Figure 6:
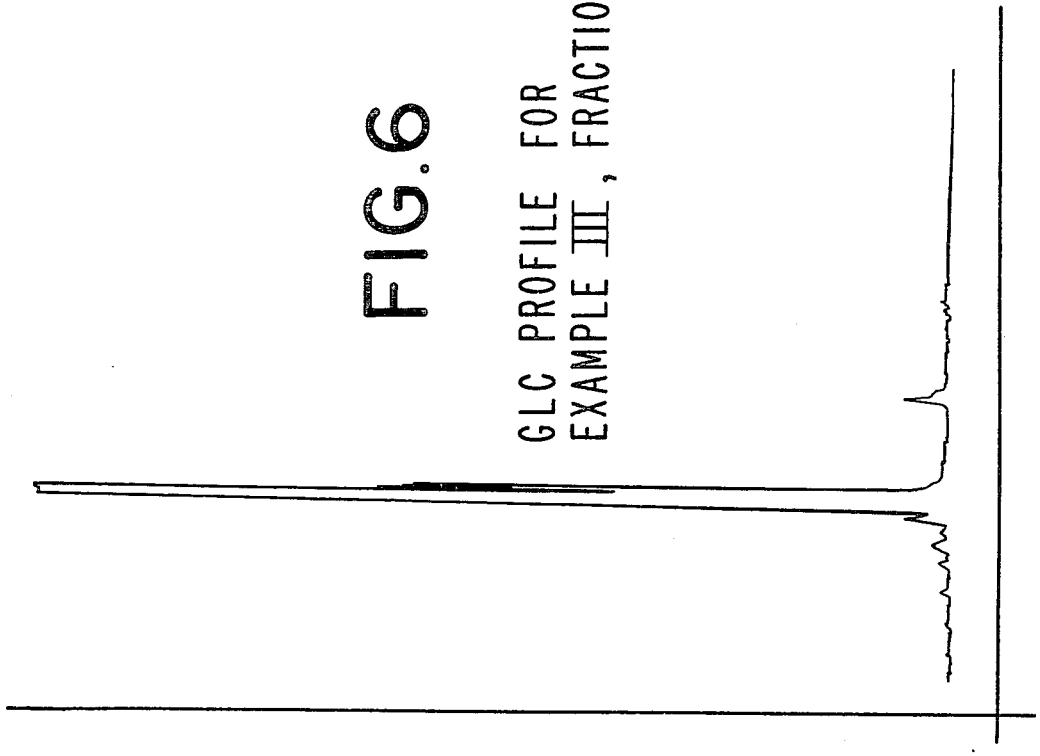
FIG. 6 is the GLC profile for fraction 5 produced according to Example III containing 1,3,5,5-tetramethyl-2-oxabicyclo[2.2.2]octane.
Figure 5:
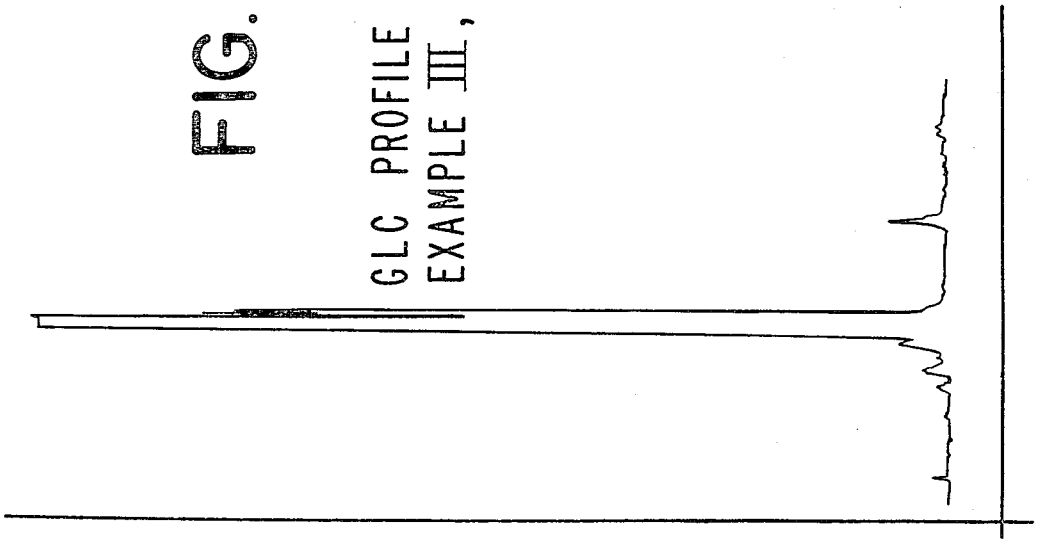
FIG. 5 is the GLC profile for fraction 4 produced according to Example III containing 1,3,5,5-tetramethyl-2-oxabicyclo[2.2.2]octane.

FIG. 3 sets forth the GLC profiles for fraction 2 above. FIG. 4 sets forth the GLC profile for fraction 3 above. FIG. 5 sets forth the GLC profile for fraction 4 above. FIG. 6 sets forth the GLC profile for fraction 5 above.

Figure 7:
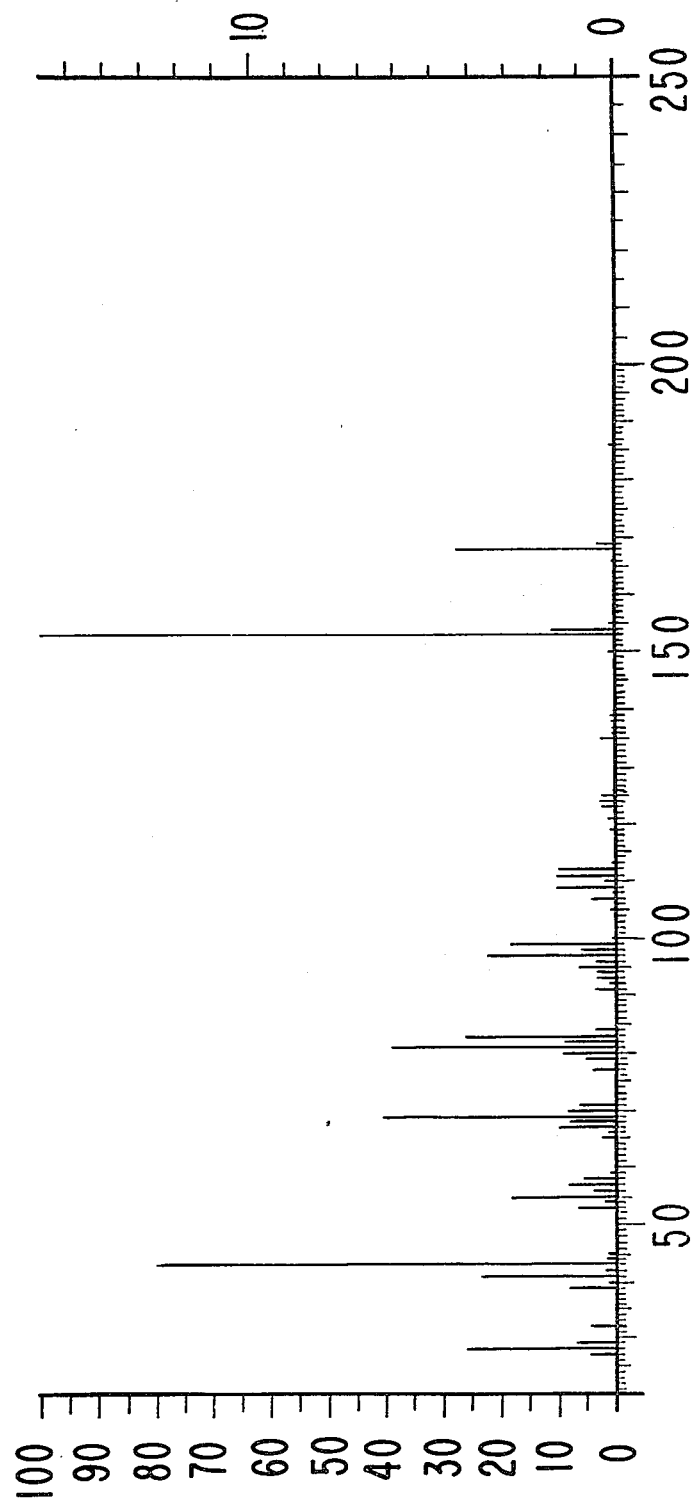
FIG. 7 is the mass spectrum of 1,3,5,5-tetramethyl-2-oxabicyclo[2.2.2]octane produced according to Example III.
Figure 8:
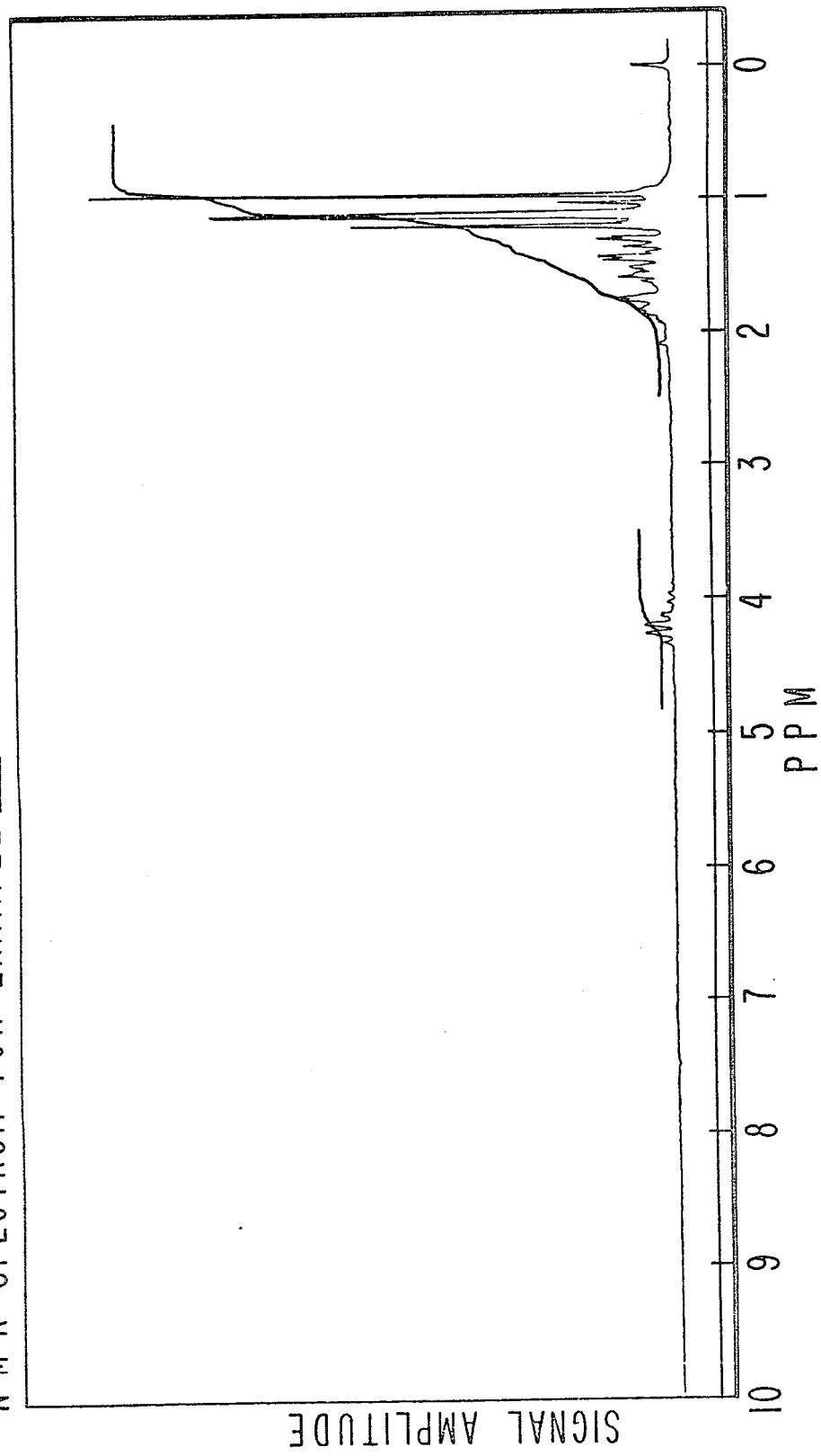
FIG. 8 is the NMR spectrum for 1,3,5,5-tetramethyl-2-oxabicyclo[2.2.2]octane produced according to Example III.
Figure 9:
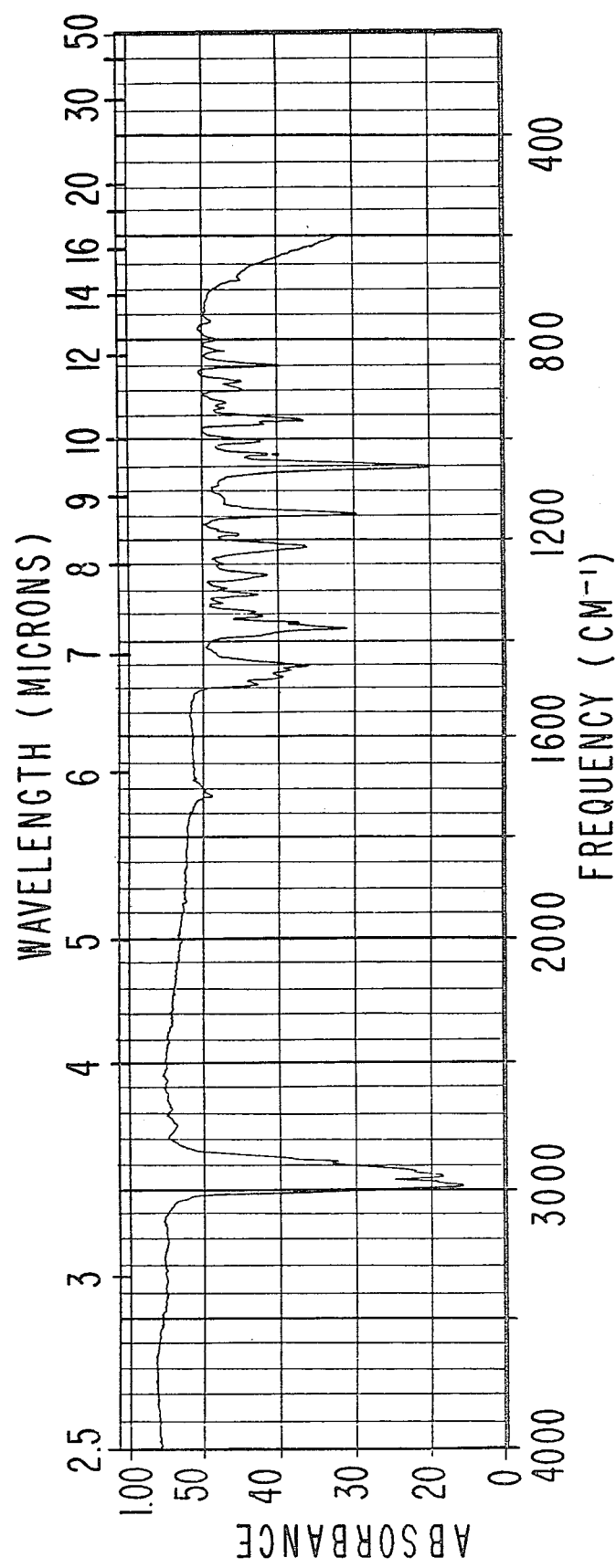
FIG. 9 is the infra-red spectrum for 1,3,5,5-tetramethyl-2-oxabicyclo[2.2.2]octane produced according to Example III.

FIG. 7 sets forth the mass spectrum for 1,3,5,5-tetramethyl-2-oxabicyclo [2.2.2]octane. FIG. 8 sets forth the NMR spectrum for 1,3,5,5-tetramethyl-2-oxabicyclo [2.2.2]octane. FIG. 9 sets forth the infra-red spectrum for 1,3,5,5-tetramethyl-2-oxabicyclo [2.2.2]octane.

EXAMPLE IV

Toothpaste Flavor Formulations

The following basic toothpaste flavor formulation is prepared:

| Ingredients | Parts by Weight |
| --- | --- |
| Cardamon Oil | 0.2 |
| Clove Oil | 1.0 |
| Spearmint Oil | 2.0 |
| Peppermint Oil | 96.8 |

This flavor formulation is divided into three portions. Eight parts by weight of the first portion is combined with 2 parts by weight of anethol. Eight parts by weight of the second portion of this flavor is combined with 2 parts by weight of 1,3,5,5-tetramethyl-2-oxabicyclo[2.2.2]octane prepared according to Example III. Eight parts by weight of the third portion of this flavor is left alone. Each of the three flavors are compared in water at the rate of 10 ppm and evaluated by a bench panel. Each of the three flavors has a sweet anise-like character but the flavor containing the 1,3,5,5-tetramethyl-2-oxabicyclo[2.2.2]octane produced according to Example III produces, in addition, a full eucalyptus oil related note missing in the other two flavors. Accordingly, the bench panel considers the flavor containing the 1,3,5,5-tetramethyl-2-oxabicyclo[2.2.2]octane as being better and more suitable as a toothpaste flavor with a unique flavor effect. The toothpaste flavor formulations prepared as above are added to toothpastes at the rate of 0.01% by weight of flavor formulation in the toothpaste. The toothpaste used is unflavored Crest ® Toothpaste (trademark product of Proctor and Gamble Company of Cincinnati, Ohio). The results of a bench panel test wherein toothbrushing is carried out in a normal manner are that the toothpaste containing the 1,3,5,5-tetramethyl-2-oxabicyclo[2.2.2]octane imparts a pleasant eucalyptus oil-like aroma and taste and aftertaste, whereas the toothpastes not containing the 1,3,5,5-tetramethyl-2-oxabicyclo[2.2.2]octane do not so impart such a pleasant flavor.

EXAMPLE V

Eucalyptus Oil Flavor Formulation

The following eucalyptus oil flavor formulation is prepared:

| Ingredients | Parts by Weight |
|---|---|
| Natural Eucalyptus Oil | 0.8 |
| Cineole | 0.3 |
| Carvone | 0.25 |
| Alpha-terpinene | 0.25 |
| Alpha Fenchyl Alcohol | 0.25 |
| Limonene | 0.35 |
| Linalool | 0.25 |
| Nootkatone | 0.25 |
| Neryl Acetate | 0.25 |

The flavor formulation is divided into two portions. Four parts per million of 1,3,5,5-tetramethyl-2-oxabicyclo[2.2.2]octane prepared according to Example III is added to 200 parts per million of the first portion of the eucalyptus oil flavor prepared above; and to the second portion of the eucalyptus oil flavor nothing is added. A definite aroma improvement, a more natural eucalyptus oil aroma and taste, as well as a pleasant sour effect and generally improved taste with citrusy nuances is created as a result of addition of the 1,3,5,5-tetramethyl-2-oxabicyclo[2.2.2]octane to the eucalyptus oil flavor. In general, the 1,3,5,5-tetramethyl-2-oxabicyclo[2.2.2]octane supplies a natural citrusy/eucalyptus oil note to this eucalyptus oil flavor. The flavor is additionally improved still further with addition of 2 parts per million of fenchyl ethyl ether prepared according to Application for U.S. Letters Patent, Ser. No. 872,937, now U.S. Pat. No. 4,131,687.

EXAMPLE VI

A. Powder Flavor Formulation

20 Grams of the flavor composition of Example V is emulsified in a solution containing 300 gm gum acacia and 700 gm water. The emulsion is spray-dried with a Bowen Lab Model Drier utilizing 260 c.f.m. of air with an inlet temperature of 500° F., an outlet temperature of 200° F. and a wheel speed of 50,000 rpm.

B. Sustained Release Flavor

The following mixture is prepared:

| Ingredients | Parts by Weight |
|---|---|
| Liquid Eucalyptus Oil Flavor Composition of Example V | 20 |
| Propylene glycol | 9 |
| Cab-O-Sil® M-5 (Brand of Silica produced by the Cabot Corporation of 125 High Street, Boston, Mass. 02110; Physical Properties: Surface Area: 200 m²gm Nominal particle size: 0.012 microns Density: 2.3 lbs/cu.ft.) | 5.00 |

The Cab-O-Sil is dispersed in the liquid Eucalyptus oil flavor compositions of Example V with vigorous stirring, thereby resulting in a viscous liquid. 71 Parts by weight of the powder flavor composition of Part A, supra, is then blended into the said viscous liquid, with stirring, at 25° C. for a period of 30 minutes resulting in a dry, free flowing sustained release flavor powder.

EXAMPLE VII 10 parts by weight of 50 Bloom pigskin gelatin is added to 90 parts by weight of water at a temperature of 150° F. The mixture is agitated until the gelatin is completely dissolved and the solution is cooled to 120° F. 20 parts by weight of the liquid eucalyptus oil flavor composition of Example V is added to the solution which is then homogenized to form an emulsion having the particle size typically in the range of 2-5 microns. This material is kept at 120° F. under which conditions of the gelatin will not jell.

Coacervation is induced by adding slowly and uniformly 40 parts by weight of a 20% aqueous solution of sodium sulphate. During coacervation the gelatin molecules are deposited uniformly about each oil droplet as a nucleus.

Gelatin is effected by pouring the heated coacervate mixture into 1,000 parts by weight of 7% aqueous solution of sodium sulphate at 65° F. The resulting jelled coacervate may be filtered and washed with water at temperatures below the melting point of gelatin to remove the salt.

Hardening of the filtered cake, in this example, is effected by washing with 200 parts by weight of 37% solution of formaldehyde in water. The cake is then washed to remove residual formaldehyde.

EXAMPLE VIII

Chewing Gum

100 Parts by weight of chicle are mixed with 4 parts by weight of the flavor prepared in accordance with Example VI. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting eucalyptus oil flavor.

EXAMPLE IX

Chewing Gum

100 Parts by weight of chicle are mixed with 18 parts by weight of the flavor prepared in accordance with Example VII. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting eucalyptus oil flavor.

EXAMPLE X

Toothpaste Formulation

The following separate groups of ingredients are prepared:

| Parts by Weight | Ingredient |
|---|---|
| Group "A" | |
| 30.200 | Glycerine |
| 15.325 | Distilled Water |
| .100 | Sodium Benzoate |

-continued

| Parts by Weight | Ingredient |
| --- | --- |
| .125 | Saccharin Sodium |
| .400 | Stannous Fluoride |
| Group "B" | |
| 12.500 | Calcium Carbonate |
| 37.200 | Dicalsium Phosphate (Dihydrate) |
| Group "C" | |
| 2.000 | Sodium N-Lauroyl Sarcosinate (foaming agent) |
| Group "D" | |
| 1.200 | Flavor Material of Example VI |
| 100.00 - TOTAL | |

PROCEDURE:
1. The ingredients in Group "A" are stirred and heated in a steam jacketed kettle to 160° F.
2. Stirring is continued for an additional three to five minutes to form a homogeneous gel
3. The powders of Group "B" are added to the gel, while mixing, until a homogeneous paste is formed
4. With stirring, the flavor of "D" is added and lastly the sodium-n-lauroyl sarcosinate
5. The resultant slurry is then blended for one hour. The completed paste is then transferred to a three roller mill and then homogenized, and finally tubed.

The resulting toothpaste when used in a normal toothbrushing procedure yields a pleasant eucalyptus oil flavor, of constant strong intensity throughout said procedure (1–1.5 minutes).

EXAMPLE XI

Chewable Vitamin Tablets

The flavor material produced according to the process of Example VI is added to a Chewable Vitamin Tablet. Formulation at a rate of 10 gm/Kg which Chewable Vitamin Tablet formulation is prepared as follows:

In a Hobart Mixer, the following materials are blended to homogeneity:

| | Gms/1000 Tablets |
| --- | --- |
| Vitamin C (ascorbic acid) as ascorbic acid-sodium ascorbate mixture 1:1 | 70.11 |
| Vitamin B$_1$ (thiamine mononitrate) as Rocoat ® thiamine mononitrate 33⅓% (Hoffman La Roche) | 4.0 |
| Vitamin B$_2$ (riboflavin) as Rocoat ® riboflavin 33⅓% | 5.0 |
| Vitamin B$_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33⅓% | 6.6 |
| d-Biotin | 0.044 |
| Flavor of Example VI | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 gm dry Vitamin A Acetate and 0.6 gm Vitamin D are then added as beadlets. The entire blend is then compressed using concave punches at 0.5 gm each.

Chewing of the resultant tablets yields a pleasant, long-lasting, consistently strong eucalyptus oil flavor with lime nuances for a period of 12 minutes.

EXAMPLE XII

A tobacco blend is made up by mixing the following materials:

| Ingredient | Parts by Weight |
| --- | --- |
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes, and the following formulation is compounded and incorporated into each of these cigarettes:

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with 1,3,5,5tetramethyl-2-oxabicyclo[2.2.2]octane produced according to Example III at 100 ppm per cigarette. Another one-third of these model cigarettes are treated in the filter with 1,3,5,5-tetramethyl-2-oxabicyclo[2.2.2]octane produced according to Example III at the rate of $2 \times 10^{-5}$ gm. When evaluated by paired comparison, the cigarettes treated both in the tobacco and in the filter with 1,3,5,5-tetramethyl-2-oxabicyclo[2.2.2]octane are found, in smoke flavor, to be sweeter, earthier, cooling and more citrusy and more tobacco-like with enhanced fruity nuances in both the main stream and in the side stream.

EXAMPLE XIII

Perfumed Liquid Detergent

Concentrated liquid detergents (Lysine salt of n-dodecylbenzene sulfonic acid as more specifically described in U.S. Pat. No. 3,948,818 issued on Apr. 6, 1976) with minty, camphoraceous aroma nuances with woody and piney undertones are prepared containing 0.10%, 0.15% and 0.20% of the 1,3,5,5-tetramethyl-2-oxabicyclo[2.2.2]octane prepared according to Example III. They are prepared by adding and homogeneously mixing the appropriate quantity of 1,3,5,5-tetramethyl-2-oxabicyclo[2.2.2]octane prepared according to Example III in the liquid detergent. The detergents all possess excellent minty and camphoraceous aromas with woody and piney undertones, the intensity increasing with greater concentrations of perfume material of Example III.

EXAMPLE XIV

Preparation of a Cologne and Handkerchief Perfume

The 1,3,5,5-tetramethyl-2-oxabicyclo[2.2.2]octane prepared according to Example III is incorporated into cologne at concentrations of 2.0%, 2.5%, 3.0%, 3.5%, 4.0%, 4.5%, and 5.0% in 85%, 90% and 95% aqueous food grade ethanol; and into a handkerchief perfume at concentrations of 15%, 20%, 25%, and 30% (in 85%, 90%, and 95% aqueous food grade ethanol). A distinctive and definite minty and camphoraceous aroma with woody and piney undertones is imparted to the cologne and to the handkerchief perfume at all of the levels indicated.

EXAMPLE XV

Preparation of Soap Composition

One hundred grams of soap chips are mixed with one gram of 1,3,5,5-tetramethyl-2-oxabicyclo[2.2.2]octane, 1.5 grams of 1,3,5,5-tetramethyl-2-oxabicyclo[2.2.2]octane, 2.0 grams of 1,3,5,5-tetramethyl-2-oxabicyclo[2.2.2]octane and 2.5 grams of 1,3,5,5-tetramethyl-2-oxabicyclo[2.2.2]octane until homogeneous compositions are obtained. In each of the cases, the homogeneous compositions are heated under three atmospheres pressure at 180° C. for a period of three hours and the resulting liquids are placed in soap molds. The resulting soap cakes, on cooling, manifest minty, camphoraceous aromas with woody and piney undertones.

EXAMPLE XVI

Preparation of a Solid Detergent Composition

A detergent is prepared from the following ingredients according to Example I of Canadian Patent 1,007,948:

|  | Percent by Weight |
|---|---|
| "Neodol 45-11" (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed with 0.10, 0.15, 0.20, 0.25, 0.30 and 0.50 grams each of the 1,3,5,5-tetramethyl-2-oxabicyclo[2.2.2]octane produced according to Example III. Each of the detergent samples has an excellent minty and camphoraceous aroma with woody and piney undertones imparted by the 1,3,5,5-tetramethyl-2-oxabicyclo[2.2.2]octane produced according to Example III.

EXAMPLE XVII

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent
   1 percent of 1,3,5,5-tetramethyl-2-oxabicyclo[2.2.2]octane prepared according to Example III.

A fabric-softening composition prepared as set forth above having a minty and camphoraceous aroma with woody and piney undertones essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The minty and camphoraceous aroma with woody and piney undertones is imparted in a pleasant manner to the head space in the dryer on operation thereof using the said dryer added fabric softening nonwoven fabric.

EXAMPLE XVIII

A liquid detergent composition is prepared according to Example IV of United Kingdom Patent 1,498,520 whereby the following ingredients are admixed:

| Ingredient | Weight % |
|---|---|
| Coconut alcohol ethoxylate | 30% |
| Linear alkyl benzene sulfonate, triethanolamine salt (alkyl = $C_{11.8}$ avg.) | 10% |
| Potassium chloride | 3% |
| Triethanolamine | 3% |
| Triethanolammonium citrate | 2% |
| Ethyl alcohol | 5% |
| Soil release ether "D" | 1.0% |
| 1,3,5,5-tetramethyl-2-oxabicyclo-[2.2.2]octane produced according to Example III | 3.0% |
| Water | Balance |

The soil release ether "D" is defined according to Table II on page 15 of United Kingdom Pat. No. 1,498,520.

This composition is prepared by admixing all of the ingredients exclusive of soil release ether "D" and agitating the mixture until all electrolytes are dissolved. Soil release ether "D" is then admixed with the solution in the form of a dry powder which passes through a 150 mesh standard sieve. The resulting composition is in the liquid state and is easily pourable. The composition is found not to redden on contact with plastic bottles, does not gel when diluted with water and has a long-lasting aroma composition described as minty and camphoraceous with a woody and piney undertone when 1,3,5,5-tetramethyl-2-oxabicyclo[2.2.2]octane is added thereto.

This composition is added to an aqueous laundering bath at a concentration of 0.20% (weight) at a temperature of 55° C., water hardness 7 grains/gallon and a pH of 10.0. Polyester and mixed polyester/cotton fabrics are laundered in the bath for a period of 10 minutes after which the fabrics are thoroughly rinsed with fresh water and dried at ambient temperatures. The fabrics are provided with a soil release finish. The head space above the fabrics has a pleasant faint aroma being described as minty and camphoraceous with a woody and piney undertone.
What is claimed is:
1. The compound having the structure:
* * * * *